United States Patent [19]

Diaz et al.

[11] Patent Number: 5,057,629

[45] Date of Patent: Oct. 15, 1991

[54] PROCESS FOR REDUCING ISOPROPYL ALCOHOL IN DIISOPROPYL ETHER

[75] Inventors: Zaida Diaz; David I. Saletan, both of Houston, Tex.

[73] Assignee: Shell Oil Company, Houston, Tex.

[21] Appl. No.: 531,273

[22] Filed: May 31, 1990

Related U.S. Application Data

[63] Continuation-in-part of Ser. No. 345,583, May 1, 1989, abandoned.

[51] Int. Cl.$^5$ .............................................. C07C 41/36
[52] U.S. Cl. .................................................... 568/699
[58] Field of Search ........................................ 568/699

[56] References Cited

U.S. PATENT DOCUMENTS

| | | | |
|---|---|---|---|
| 2,556,248 | 6/1951 | Amick Jr. ............................. 202/42 |
| 4,182,914 | 1/1980 | Imaizumi ............................. 568/697 |
| 4,352,945 | 10/1982 | Bezman ............................... 568/899 |
| 4,405,822 | 9/1983 | Bezman ............................... 568/899 |
| 4,504,688 | 3/1985 | Herwig et al. ....................... 568/697 |

FOREIGN PATENT DOCUMENTS 1459242 12/1976 United Kingdom .
1574035 9/1980 United Kingdom .

*Primary Examiner*—Howard T. Mars
*Attorney, Agent, or Firm*—Ronald R. Reper

[57] ABSTRACT

A process is disclosed for selectively sorbing contaminating amounts of isopropyl alcohol from diisopropyl ether by contacting with a high surface area strong acid type cation exchange resin in the hydrogen form, preferably having a mean pore diameter in the range from about 40 to about 259 Angstroms.

6 Claims, 2 Drawing Sheets

PROCESS FOR REDUCING ISOPROPYL ALCOHOL IN DIISOPROPYL ETHER

This application is a continuation-in-part application of our copending application Ser. No. 07/345,583 filed May 1, 1989, now abandoned.

BACKGROUND OF THE INVENTION

The present invention relates to a process for reducing isopropyl alcohol impurity in diisopropyl ether. More particularly it relates to reducing levels of isopropyl alcohol in crude diisopropyl ether by contacting with certain high surface area strongly acidic cation exchange resins at mild conditions to adsorb said impurity from diisopropyl ether.

Diisopropyl ether is a chemical of commerce. It is used as an industrial solvent, reaction medium, starting material for chemicals such as organic nitrates and isopropyl benzenes, and as a blending component for gasolines. Most diisopropyl ether is produced as the result of byproduct formation in the acid catalyzed reaction of propylene and water to manufacture isopropyl alcohol. By selection of process conditions it is possible to produce diisopropyl ether containing a small amount, i.e. less than about 10% by weight of isopropyl alcohol as impurity. A wide variety of acidic catalysts are known for the reaction including e.g. sulphuric acid, phosphoric acid (typically on a carrier such as diatomaceous earth), phosphoric pentoxide, boric acid, hydrochloric acid, certain silicotungstates and highly acidic cation exchange resins. Operating conditions include temperatures from about 120° C. to about 300° C. and pressures from about 25 to about 300 atmospheres. Generally the use of lower temperatures and higher pressures tend to favor diisopropyl ether formation. Process schemes employing either chemical grade (95 mol %) or refinery grade (60 to 85 mol %) propylene have been commercialized.

Depending upon the particular catalyst and operating conditions the crude ether formed by hydration of propylene and water by either the direct, or indirect i.e. esterification by acid followed by hydrolysis route, may contain in addition to alcohol, small amounts of water, polymers and ketones, particularly acetone.

It is known from U.S. Pat. No. 2,556,248 to purify ethers by multiple distillations to a purity of about 99.5% by weight and then remove the remaining impurities by adsorption on silica gel. However, a lower cost facility could be devised if a suitable adsorptive material were found that could more effectively treat a less pure ether starting material. Such a material has now been found. The invention provides a process employing it to reduce the impurities in diisopropyl ether.

SUMMARY OF THE INVENTION

Figure 1:
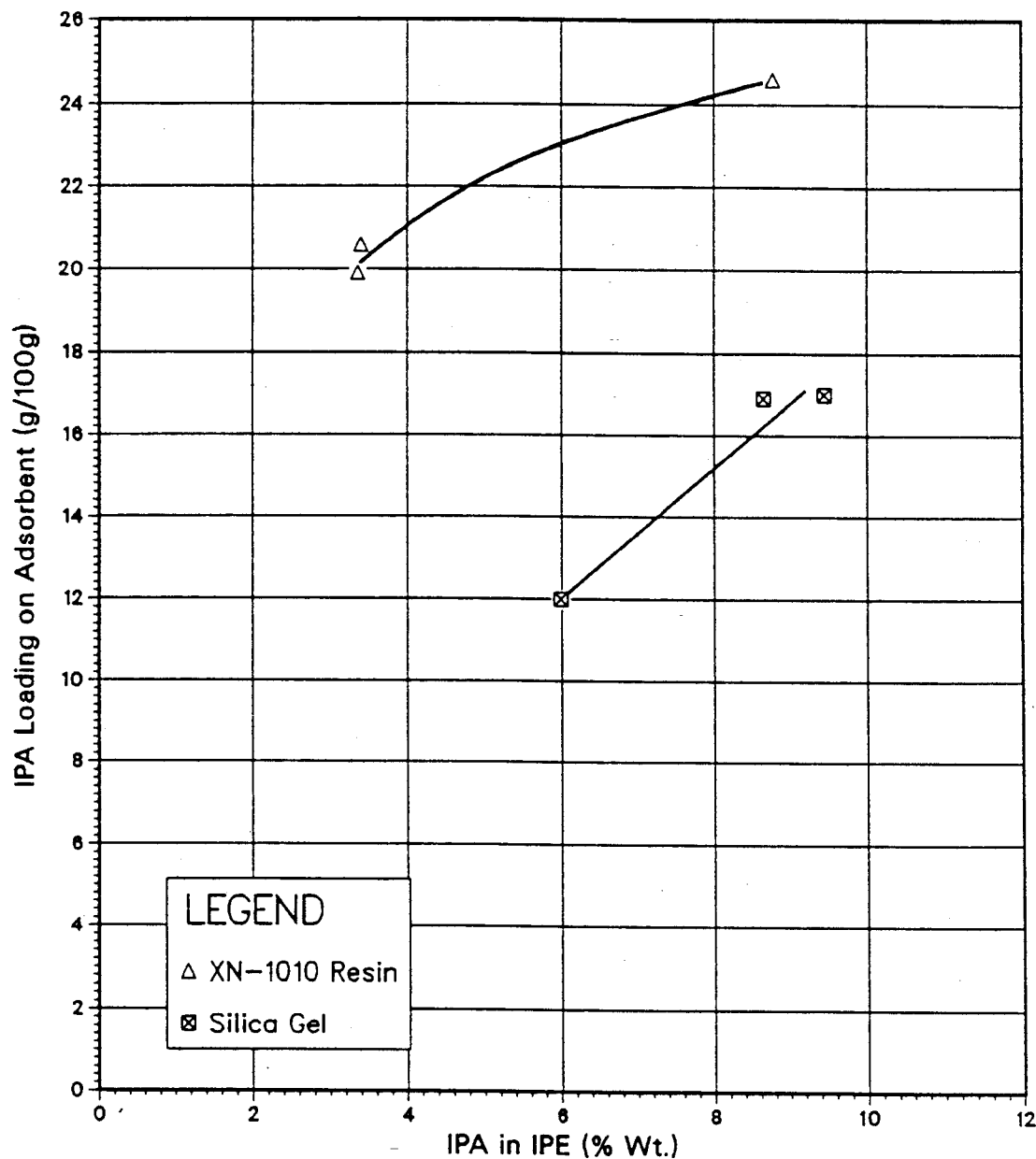
FIG. 1 graphically compares the sorbent properties of a resin according to the invention with a silica gel adsorbent.

The present invention relates to a process for reducing contaminating amounts of isopropyl alcohol in diisopropyl ether which comprises contacting as feed diisopropyl ether containing up to about 10% by weight of isopropyl alcohol in a contact zone at a temperature from about 10° C. to about 30° C. and a pressure from about 1 to about 3 atmospheres with a fixed bed of strong acid type cation exchange resin said resin being in the hydrogen form and having a high surface area to sorb the alcohol, and passing the diisopropyl ether having reduced contaminant from said contact zone.

DESCRIPTION OF PREFERRED EMBODIMENTS

The process of the present invention may be used to batch treat crude diisopropyl ether, or it may suitably be employed in combination with a process producing primarily isopropyl alcohol. Most advantageously it is employed in combination with a continuous process for producing primarily diisopropyl ether. Typically diisopropyl ether and/or isopropyl alcohol, also referred to herein as isopropanol, is produced by the catalyzed reaction of propylene, also referred to herein as propene, with water. A molar excess of water is used when the alcohol product is desired. The crude reaction product generally contains water, isopropyl alcohol, diisopropyl ether, propylene, propane and any $C_4$ hydrocarbons as may have been present in the feed. Conventionally this crude product is passed through one or more gas-liquid separators to separate the gases, i.e. propane, unreacted propylene and trace $C_4$ hydrocarbons from the liquids, i.e. water, isopropyl alcohol and diisopropyl ether.

The crude liquid product is generally treated to neutralize or remove any acids, e.g. by caustic wash, ion exchange and the like, and the treated product is passed to a distillation column. The distillation column generally is operated at near atmospheric pressure and at a temperature so that the overhead is primarily diisopropyl ether which also contains a minor amount e.g. up to about 10%, and more preferably less than 5% by weight of isopropyl alcohol and may contain some water. The bottoms from this distillation, containing primarily isopropyl alcohol and water and water soluble impurities are then processed in any of a variety of ways known in the art to dehydrate and recover the isopropyl alcohol.

The overhead from the distillation, which is primarily diisopropyl ether is contacted with a strong acid type cation exchange resin in the hydrogen form and having a high surface area, i.e. at least about 40 square meters per gram and preferably of at least about 400 square meters per gram, to selectively sorb the alcohol. It is an advantage of the present invention that very mild conditions are used. Suitable temperatures are from about 10° C., preferably 15° to 25°; suitable pressures are from about 1 to about 3 atmospheres.

The acidic cation exchange resin employed in the process according to the invention is preferably a macroreticular resin having a highly porous structure with an average pore diameter from about 40 to about 250 Angstroms, more preferably from about 40 to about 80 Anstroms, and an average particle size in the range from about 0.3 to about 1.2 mm. The highly acidic resin will preferably have a sulfonic acid functionality. Very good results were obtained with Amberlyst XN-1010, manufactured by Rohm and Haas, the preferred adsorbent in the contacting step.

The sorbent contacting step is suitably employed in a continuous process by using a plurality of sorption units suitably interconnected in parallel flow, so that as one unit is onstream to contact the crude ether feed and reduce the impurities therein, another is being regenerated. The resin adsorbent may be regenerated by elution with a polar solvent such as water at temperatures less than about 80° C. at atmospheric or subatmospheric pressure, followed by desorption of the elution solvent by any conventional method such as flowing inert gas through the sorbent bed at an elevated temperature up to about 80° C.

The following examples are merely illustrative and are not intended to constitute a limitation on the invention which is defined in the appended claims.

EXAMPLES

A number of adsorbents were tested for their ability to remove isopropanol at high concentration i.e. about 10% by weight from diisopropyl ether at mild conditions. In a first test the adsorbents tested were cation exchange resin Amberlyst XN-1010 in hydrogen form and Silica Gel Grade 12, 28×200 mesh, commercially available from Aldrich Chemical. These adsorbents were predried at 80° C. under a vacuum of about 10 mm Hg for a period of about 16 hours.

Adsorption data were obtained in conventional bottle tests. Diisopropyl ether containing about 10% by weight isopropyl alcohol was contacted with the adsorbents at various liquid to solid ratios. All experiments were done at 23° C., and the contact time was about 16 hours. After the contacting period the liquid was analyzed for isopropyl alcohol content by gas chromatography. The loading of isopropanol on the adsorbents was calculated from the change in the concentration of isopropyl alcohol in the diisopropyl ether due to the contact with the adsorbents. The results of these experiments are shown graphically in FIG. 1 wherein it is found that a high surface area macroreticular resin according to the invention is a far better adsorbent than silica gel for reducing the isopropanol content of the diisopropyl ether.

Figure 2:
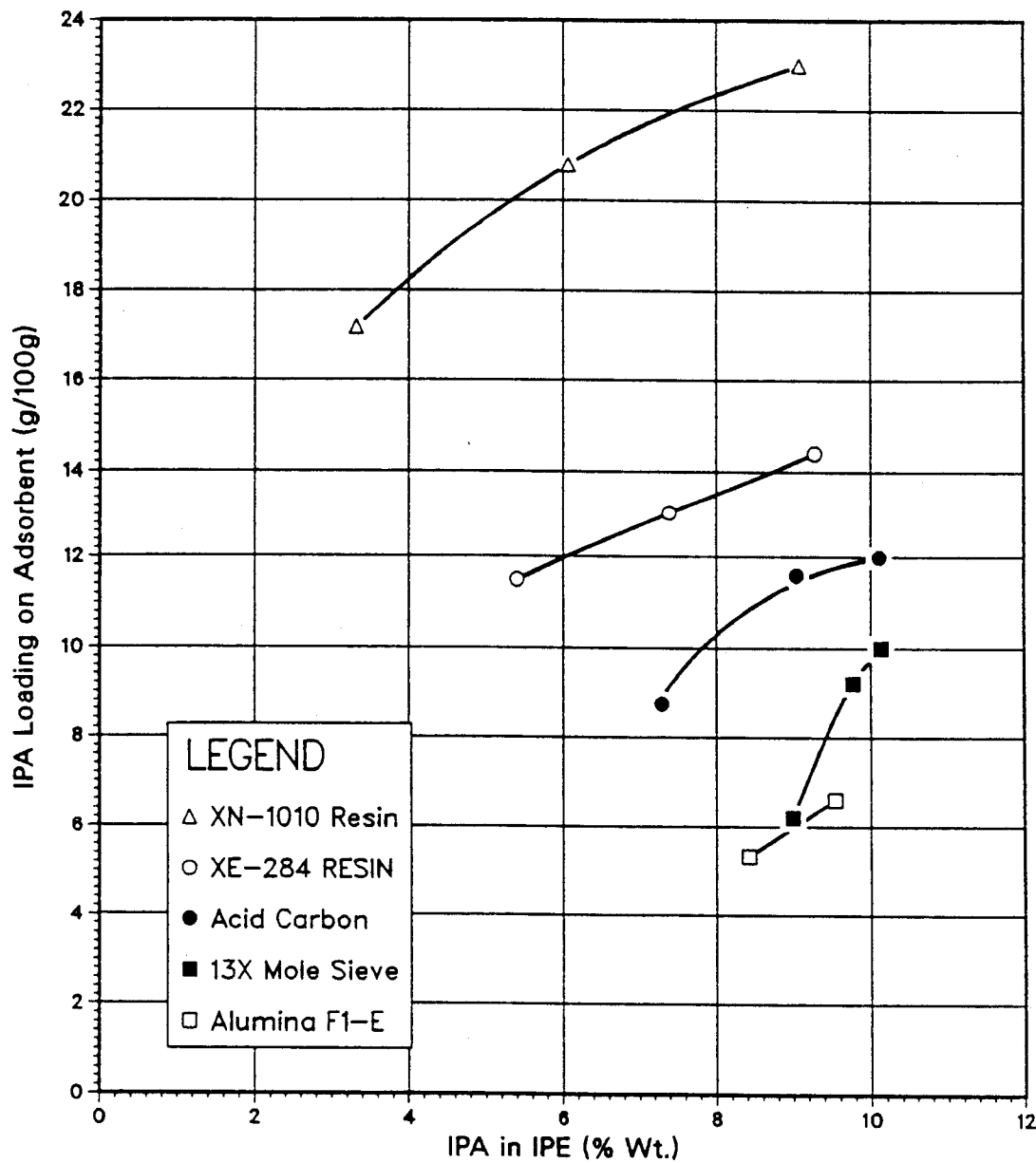
FIG. 2 graphically compares the sorbent properties of two resins according to the invention with other conventional adsorbents.

A variety of adsorbents were tested according to the foregoing procedure except that these adsorbents were predried for a shorter period, i.e. 3 hours. The adsorbents tested were: alumina marketed under the trade designation F1-E by Alcoa; 13X molecular sieve; activated carbon which had been pretreated with a strong oxidizing acid mixture of concentrated sulfuric acid and concentrated nitric acid (2:1 volume ratio) for a period of about 25 minutes followed by water washing and drying at 150° C. for 3 hours; and cation exchange resins Amberlyst XN-1010 and Amberlite XE-284 in their hydrogen form, both of said resins marketed by Rohm and Haas. Prior to testing, the adsorbents were dried in a vacuum oven at 80° C. for about 3 hours. Results are shown in FIG. 2.

The best adsorbents are both of the high surface area macroreticular cation resins, particularly Amberlyst XN-1010. This resin is described by the supplier as a sulfonated, crosslinked, polystyrene type resin supplied in its hydrogen form as spherical particles having a majority of its sulfonic acid groups at or close to the internal surface of the resin. Other properties include a porosity of 47%, surface area of 540 square meters per gram, mean pore diameter of 50 Angstrom units and a cation exchange capacity of 3.3 milliequivalents/gram.

A number of resin adsorbents including a strong base, a weak acid and two strong acid types of differing surface area were tested for their ability to remove isopropanol at high concentration, i.e., about 10% by weight from diisopropyl ether at mild conditions; the adsorbents were predried for 2 days in a vacuum over at 100° C., except for the strong base resin which was dried at somewhat lower temperature of 70° C. (to prevent deterioration of this thermally unstable resin); adsorption data were obtained in conventional bottle tests; diisopropyl ether containing about 10% by weight isopropanol was contacted with the adsorbents at two different weight ratios for a period of about 16 hours at a temperature of 23° C.; after the contacting period the liquid was analyzed for isopropanol content by gas chromatography; the loading of the isopropanol on the adsorbents was calculated from the change in the concentration of isopropanol in the diisopropyl ether due to contact with the adsorbents; the results of these experiments are shown in the following Table wherein it is found that strong base and weak acid type resins have nil capacity to reduce the isopropanol content of the diisopropyl ether, in contrast to the excellent capacity of both strong acid type resins used;

| TABLE OF ADSORPTION RESULTS | | | | |
|---|---|---|---|---|
| AD-SORBENT | TYPE | SURFACE AREA SQ M/G | WT LIQUID/ WT AD-SORBENT | IPA ADSORBED (g IPA/100 g ADS) |
| AMBERLYST XN 1010 | STRONG ACID | 540 | 3 | 20.1 (@ 3.30% IPA in DIPE) |
| | | | 20 | 26.0 (@ 8.70% IPA in DIPE) |
| AMBERLYST A-26 | STRONG BASE | 28 | 3 | NIL |
| | | | 20 | NIL |
| AMBERLYST 15 | STRONG ACID | 50 | 3 | 22.6 (@ 2.48% IPA in DIPE) |
| | | | 20 | 28.0 (@ 8.60% IPA in DIPE) |
| DUOLITE C464 | WEAK ACID | * | 3 | NIL |
| | | | 20 | NIL |

*Data not available.

Subsequent laboratory flow experiments contacting a feed of diisopropyl ether containing about 10% by weight of isopropyl alcohol with a bed of Amberlyst XN-1010 indicate that best results are obtained when using beds having a high (>15 L/D) ratio. At these high concentrations of alcohol in ether the resin beds can only treat a few bed volumes of feed per cycle, but very high bed loadings on the order of 20 g isopropanol/100 g resin were achieved. Owing to scaling factors it appears likely that a lower L/D ratio would be used in commercial operations.

What is claimed is:

1. Process for reducing contaminating amounts of isopropyl alcohol from diisopropyl ether which process comprises contacting diisopropyl ether containing up to about 10% by weight of isopropyl alcohol in a contact zone at a temperature from about 10° to about 30° C. and a pressure from about 1 to about 3 atmospheres with a bed of strong acid type cation exchange resin, said resin being in the hydrogen ion form and having a surface area of at least about 40 square meters per gram, to sorb said alcohol, passing diisopropyl ether having reduced contaminant from said contact zone, and intermittently regenerating said resins with water to displace the isopropyl alcohol from the resin, followed by removal of said water from said resin at an elevated temperature up to about 80° C.

2. Process as in claim 1, wherein said resin contains sulfonic acid groups.

3. Process as in claim 1, wherein said resin has a mean pore diameter in the range from about 40 to about 250 Angstroms.

4. Process as in claim 1, wherein said resin has a mean pore diameter in the range from about 40 to about 80 Angstroms.

5. Process as in claim 1 wherein said diisopropyl ether contains less than about 5% by weight of isopropyl alcohol.

6. Process as in claim 1 wherein said resin has a surface area of at least about 400 square meters per gram.

* * * * *